US006869466B2

(12) United States Patent
Day et al.

(10) Patent No.: US 6,869,466 B2
(45) Date of Patent: Mar. 22, 2005

(54) CUCURBITURILS AND METHOD FOR BINDING GASES AND VOLATILES USING CUCURBITURILS

(75) Inventors: Anthony Ivan Day, Captains Flat (AU); Alan Peter Arnold, Flynn (AU); Rodney John Blanch, Holt (AU)

(73) Assignee: Unisearch Limited, Sydney (AU)

( * ) Notice: Subject to any disclaimer, the term of this patent is extended or adjusted under 35 U.S.C. 154(b) by 0 days.

(21) Appl. No.: 10/301,874

(22) Filed: Nov. 22, 2002

(65) Prior Publication Data

US 2003/0140787 A1 Jul. 31, 2003

Related U.S. Application Data

(63) Continuation-in-part of application No. 09/959,770, filed as application No. PCT/AU00/00412 on May 5, 2000, now Pat. No. 6,793,839.

(30) Foreign Application Priority Data

May 7, 1999 (AU) ............................................. PQ0232
Nov. 22, 2001 (AU) ............................................. PR9031

(51) Int. Cl.$^7$ ........................ B01D 53/46; B01D 53/62; B01D 53/72; B01D 53/73; B01D 53/76
(52) U.S. Cl. ............................ 95/205; 95/226; 95/230; 95/232; 95/233; 95/237; 95/238; 95/239
(58) Field of Search ......................... 95/205, 226, 230, 95/232, 233, 237, 238, 239

(56) References Cited

U.S. PATENT DOCUMENTS 6,365,734 B1     4/2002  Kim et al.
2003/0212268 A1 * 11/2003  Kim et al. .................. 540/452

FOREIGN PATENT DOCUMENTS

| DE | 10126394 A1 * | 12/2002 | ............ B01J/20/00 |
| EP | 1 094 065 A2 | 4/2001 | |
| EP | 1210966 A1 * | 6/2002 | ........... B01D/39/16 |
| JP | 11217557 A * | 8/1999 | ............ C09K/3/00 |

OTHER PUBLICATIONS

Grant, Julius (Editor), "Hackh's Chemical Dictionary" Fourth Edition (McGraw–Hill Book Company, New York, 1972), p. 717, "volatile" & "volatilization" & "volatilize."*
Lewis, Richard J., Sr. (Revised by), "Hawley's Condensed Chemical Dictionary" Fourteenth Edition (John Wiley & Sons, Inc., New York, 2001), p. 1169, "volatility."*
JPO abstract for JP11–21557–A, Taketsuji (Aug. 10, 1999).*
USPTO obtained translation of EP 1210966 A1.*
Cintas, P. "Cucurbituril: Supramolecular Perspectives for an Old Ligand" "Journal of Inclusion Phenomena and Molecular Recognition in Chemistry" 17:205–220, 1994.*

Abstract for WO 02/096553 A2.*
Derwent abstract ACC–NO.: 2002601193, for EP 1210966A1 (Jun. 5, 2002) Blum et al.*
Mock, et al. "Host–Guest Binding Capacity of Cucurbituril", J. Org. Chem., 1983, 48 (20), 3618–3619.*
Flinn, et al. "Decamethylcucurbit[5]uril", Angew. Chem. Int. Ed. Engl., 1992,31,(11), 1475–1477.*
Kim et al. "New Cucurbituril Homologues: Syntheses, Isolation, Characterization, and X–ray Crystal Structures of Cucurbit[n]uril (n=5, 7, and 8)" J. Am. Chem. Soc., 2000, 122, 540–541.*
USPTO obtained translation of DE 4001139 (Jan. 25, 1990), Buschmann, et al.*
Dantz et al. "Complexation of Volatile Organic Molecules from the Gas Phase with Cucurbituril and β–Cyclodextrin", Supramolecular Chemistry, vol. 9, pp. 79–83, 1998.
Kellensberger et al., "Encapsulation of N2, O2, Methannol, or Acetonitrile by Decamethylcucurbit[5]uril . . . " J. Am. Chem. Soc. 2001, 123, pp. 11316–11317, web release date Oct. 20, 2001.
Haouaj et al., "NMR Study of the reversible complexation of xenon by cucurbituril", J. Chem. Soc. Perkin Trans 2, 2001,pp. 804–807.
Haouaj et al., "NMR Investigation of the complexation of neutral guests by cucurbituril", J. Chem. Soc. Perkins Trans. 2, 2001, pp. 2104–2107.
Jeon et al., "Molecular Container Assembly Capable of Controlling Binding and Release of Its Guest Molecules . . . ", J. Am. Chem. Soc. 1996, 118, p. 9790.
Miyahara et al., "Molecular Molecular Sieves: Lid–Free Decamethylcucurbit[5]uril Absorbs and Desorbs Gases Selectively" Angew. Chem. Int. Ed. 2002, 41, No. 16, pp. 3020–3023.

* cited by examiner

*Primary Examiner*—Matthew A. Thexton
(74) *Attorney, Agent, or Firm*—Stites & Harbison PLLC; B. Aaron Schulman

(57) ABSTRACT

In accordance with the invention, there is provided a method of binding a gas or volatile compound in a cucurbituril, by contacting the gas or volatile compound with the cucurbituril to form a cucurbituril-gas/volatile complex. There is also provided a method of separating a gas or volatile compound from a mixture of compounds wherein the mixture is contacted with a cucurbituril and whereby at least some of the gas or volatile compound is bound to the cucurbituril to form a cucurbituril complex, followed by the release of at least some of the bound gas or volatile compound from that complex. The present invention is thus advantageous in that it allows use of cucurbiturils in binding gases and volatile compounds for storage, safety, delivery or other uses, such as the trapping of an unpleasant or toxic gas or volatile compound.

18 Claims, No Drawings

CUCURBITURILS AND METHOD FOR BINDING GASES AND VOLATILES USING CUCURBITURILS

CROSS-REFERENCE TO RELATED APPLICATIONS

The present application is a continuation-in-part of U.S. Ser. No. 09/959,770, filed Jan. 7, 2002, now U.S. Pat. No. 6,793,839 which is the national stage application of PCT International Application PCT/AU00/00412, filed May 5, 2000, and also claims the benefit of Australian provisional application PR9031 filed on Nov. 22, 2001.

FIELD OF THE INVENTION

The present invention relates generally to a method of binding gases and volatiles in cucurbiturils.

BACKGROUND OF THE INVENTION

Cucurbituril is the name given to a cyclic oligomer formed by linking six (6) glycoluril units via methylene bridges. However, to differentiate the various cucurbiturils, this compound is referred to in this specification as "unsubstituted cucurbit[6]uril". The substituted cucurbituril decamethylcucurbit[5]uril was first synthesised and identified in 1992 by Flinn et. al. (Angew. Chem. Int. Ed. Engl., 1992, 31, 1475). The remaining unsubstituted cucurbit[4 to 12]urils and some substituted cucurbit[4 to 12]urils, were synthesised by Day et. al. as described in the applicant's international patent application No. PCT/AU00/00412 (WO 00/68232), and in parent application Ser. No. 09/959,770, incorporated herein by reference.

Unsubstituted cucurbit[6]uril was first described in the literature in 1905 in a paper by R. Behrend, E. Meyer and F. Rusche, Leibigs Ann. Chem.; 339, 1, 1905. The macrocyclic structure of unsubstituted cucurbit[6]uril was first described in 1981 by W. A. Freeman et. al., "Cucurbituril", J. Am. Chem. Soc., 103 (1981), 7367–7368. Unsubstituted cucurbit[6]uril has a chemical formula of $C_{36}H_{36}N_{24}O_{12}$ and is a macrocyclic compound having a central cavity.

The internal cavity of unsubstituted cucurbit[6]uril has a diameter of about 550 pm, a depth of 650 pm with portals at either end about 400 pm across. This rigid cavity has been shown to have high selectively in binding a variety of medium-small molecules and in this regard reference is made to Cintas, P., J. Inclusion Phenomena and Molecular Recognition in Chemistry; 17, 205, 1994.

The preparation of unsubstituted cucurbit[6]uril has generally followed the procedure first described in the article by R. Behrend et. al. published in 1905.

In German patent no. DE 19603377, published Aug. 7, 1997, a process for synthesising unsubstituted cucurbit[6]uril is described. This process includes dissolving acetylene diurea (glycoluril) in an aqueous solution of a strong mineral acid in the presence of excess formaldehyde, with warming. The water is evaporated from the mixture to completely eliminate the water from the mixture. The remaining polymer mixture is then heated to a temperature up to 145° C. to complete the reaction. The applicants for DE 19603377 have stated that a yield of up to 82.4% of the theoretical yield can be obtained.

In German patent no. DE 4001139, the use of unsubstituted cucurbit[6]uril to remove organic compounds with hydrophobic groups, dyes, decomposition products from dyes and/or heavy metals from aqueous solutions is described. The patent actually states that a cyclic oligomer which is obtained by condensation of urea, thiourea, derivates of urea and/or derivatives of the thiourea with dialdehydes and formaldehyde is used. Although the patent states that the degree of polymerisation, n, of the cyclic oligomer varies between about 3 and about 8, the examples of the patent showing cyclic oligomers having a degree of polymerisation, n, only of 6. Example 1 shows the preparation of unsubstituted cucurbit[6]uril by heating glycoluril under reflux with formaldehyde.

Experiments conducted by the present inventors in following the procedure of Example 1 of DE 4001139 have shown that cucurbituril having 6 glycoluril units joined together is formed. In the words of DE 4001139, n=6 for this product. No evidence was found of any cyclic oligomer having a degree of polymerisation, n, other than 6. Indeed, a paper by Buschmann et. al., Inorgica Chimica Acta, 1992, 193, 93 states that under the synthetic conditions as described in DE 400 1139, only cucurbituril having a degree of polymerisation, n, of 6 is formed.

SUMMARY OF THE INVENTION

According to one aspect of the present invention, there is provided a method of binding a gas or volatile compound in a cucurbituril, said method comprising contacting the gas or volatile compound with the cucurbituril to form a cucurbituril complex of the gas or volatile compound; provided that when the volatile compound is an organic molecule, the cucurbituril is not unsubstituted cucurbit[6]uril.

According to another aspect of the present invention, there is provided a method of separating a gas or volatile compound from a mixture of compounds including the gas or volatile compound, said method comprising the steps of:

1) contacting the mixture with a cucurbituril whereby at least some of the gas or volatile compound is bound to the cucurbituril to form a cucurbituril complex of the gas or volatile compound; and 2) releasing at least some of the bound gas or volatile compound from said complex;

provided that when the volatile compound is an organic molecule, the cucurbituril is not unsubstituted cucurbit[6]uril.

The mixture of compounds including the gas or volatile compound may be in the form of a gaseous mixture containing the gas or volatile compound, or may be in the form of a liquid or solid containing the gas or volatile compound.

By "cucurbituril complex of the gas or volatile compound", it is meant that the gas or volatile compound has been taken up into the central cavity of the cucurbituril.

Preferably the cucurbituril is a substituted or unsubstituted cucurbit[n]uril where n=5 to 10. The cucurbituril may for example be unsubstituted cucurbit[n]uril where n=5 to 10. In other embodiments, the cucurbituril may be a cucurbit[s,u]uril, where s=1 to 12, u=0 to 11 and s plus u equals 4 to 12, and s and u are the number of substituted and unsubstituted glycoluril units, respectively.

The gas may for example be a hydrocarbon gas, such as methane, ethane, propane, propene, ethylene, acetylene, isobutylene, butadiene, diacetylene, or an inorganic gas such as $N_2$, $O_2$, $H_2$, Ar, Ne, CO or NO. The volatile compound may for example be a toxic vapour such as ethanediol, a fragrance such as rose oil, a functionalised hydrocarbon such as chloroform, an unpleasant odour, or a volatile biologically active compound such as certain pesticides, herbicides or pharmaceutically active compounds. Examples of volatile pharmaceutically active compounds include certain anaesthetics. Another example of a volatile compound is dioxane.

In some embodiments, the gas or volatile compound is an air pollutant such as carbon monoxide, carbon dioxide, $SO_x$ or $NO_x$ (where x=1 or 2). In other embodiments, the gas or volatile compound is a gas or volatile compound other than the air pollutants carbon monoxide, carbon dioxide, $SO_x$ or $NO_x$.

In some embodiments, when the gas or volatile compound is $N_2$, $O_2$, methanol or acetonitrile, the cucurbituril is a cucurbituril other than decamethylcucurbit[5]uril.

In some embodiments, when the gas or volatile compound is $N_2$, $O_2$, Xe or other inert gas, the cucurbituril is a cucurbituril other than unsubstituted cucurbit[6]uril.

In some embodiments, the cucurbituril is a cucurbituril other than unsubstituted cucurbit[6]uril or decamethylcucurbit[5]uril.

In some embodiments, the method involves preparing a solution, such as an aqueous solution, of the cucurbituril and contacting the gas or volatile compound, or the mixture, with said solution. In some embodiments, all the cucurbituril is dissolved in the solution. In other embodiments, the cucurbituril is partly dissolved in the solution, and partly in the form of a suspension.

In an alternative embodiment, the cucurbituril is supported on a solid support or matrix prior to contact with the gas or volatile compound, or the mixture. In another alternative embodiment, the cucurbituril is in a solid phase (without a solid support or matrix).

In those embodiments where the cucurbituril is in solution, the solution may include a solubilising agent for increasing the solubility of the cucurbituril in the solution.

For aqueous solutions, the solubilising agent may be a metal salt, for example NaCl or CsCl, an ammonium salt, for example $NH_4Cl$, an acid such as a mineral or organic acid, for example formic acid, citric acid or trifluoroacetic acid (TFA), and/or a polyhydroxylated organic compound such as sugars (for example glucose, sucrose or cyclodextrins), starch or glycerol. Other suitable solubilising agents for increasing the solubility of the cucurbituril in aqueous solutions are coordination complexes, such as hexaammine cobalt (III) chloride. Preferably the preparation of the aqueous solution of the cucurbituril is performed at a temperature of between ambient to 100° C.

In those embodiments where the cucurbituril is in solution, the step of contacting the gas or volatile compound with the cucurbituril typically involves passing the gas or volatile compound through the solution of the cucurbituril to form the cucurbituril complex. Alternatively the cucurbituril solution is exposed to an atmosphere of the gas or volatile compound.

When the mixture of compounds including the gas or volatile compound is a gaseous mixture, and the cucurbituril is in solution, the step of contacting the mixture with the cucurbituril typically involves passing the mixture through the solution of the cucurbituril. Alternatively, the cucurbituril solution is exposed to an atmosphere of the gaseous mixture.

When the mixture of compounds including the gas or volatile compound is a solid or liquid, the step of contacting the mixture with the cucurbituril typically involves dispersing or dissolving the mixture in a solution of the cucurbituril, or passing the mixture through a solution of cucurbituril, to form a cucurbituril complex of the gas or volatile compound.

Where the cucurbituril complex of the gas or volatile compound is in solution, the step of releasing the bound gas or volatile compound from the complex typically involves either purging the complex with an inert gas such as nitrogen for an extended period and/or heating the complex to a temperature sufficient to release the gas or volatile compound. The cucurbituril complex may be purged with an inert gas by passing the inert gas through the solution. Typically the complex is purged for more than about 15 minutes and/or heated to between 60 to 100° C. For some cucurbituril complexes of a gas or volatile compound, there is a slow diffusion of the bound gas or volatile compound from the complex over time. In such a case the step of releasing the bound gas or volatile compound from the complex may comprise the gradual diffusion of the gas or volatile compound from the complex at ambient temperatures.

In some embodiments of the invention, after the cucurbituril complex of the gas or volatile compound is formed in solution, the cucurbituril complex is isolated from the solution, for example, by crystallisation or precipitation using a non-solubilising solvent. For example, the cucurbituril complex may be isolated from the solution for storage, and the bound gas or volatile compound then later released from the complex.

Where the gas or volatile compound is adsorbed into solid phase cucurbituril, or a solid cucurbituril complex is isolated from solution as described in the preceding paragraph, the step of releasing the bound gas or volatile compound from the solid cucurbituril complex typically involves dissolving the complex in a solvent and heating the resultant solution to a temperature sufficient to release the gas or volatile compound. Typically the solvent is water, TFA or an aqueous salt solution, and typically the solution is heated to a temperature of from between 60 to 100° C. Alternatively, the bound gas or volatile compound may be released from the solid cucurbituril complex by purging the complex with an inert gas and/or heating the complex. For some cucurbituril complexes of a gas or volatile compound, there is a slow diffusion of the bound gas or volatile compound from the complex over time. For such a cucurbituril complex, the step of releasing the bound gas or volatile compound from the cucurbituril complex may involve the gradual diffusion of the bound gas or volatile compound from the complex at ambient temperatures.

DETAILED DESCRIPTION OF THE PREFERRED EMBODIMENTS

As used herein, the term "cucurbituril" refers to a compound of the formula I, and the term "cucurbiturils" refers to the class of compounds of the formula I:

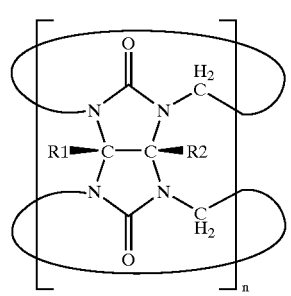

I wherein n=4 to 12, and wherein, for each glycoluril unit of the formula II:

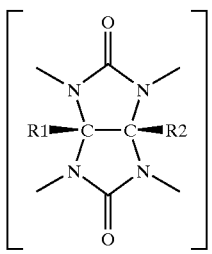

in the compound of formula I, $R_1$ and $R_2$ are the same or different and are selected from H or an optionally substituted straight chain, branched or cyclic, saturated or unsaturated hydrocarbon radical, or a heterocyclyl radical, or $R_1$ and $R_2$ together form a cyclic hydrocarbon radical. $R_1$ and $R_2$ may for example be alkyl (e.g. methyl), alkenyl, alkynyl, aryl (e.g. phenyl) or heterocyclyl (e.g. furanyl) radicals. Cucurbiturils may be prepared as described in parent application Ser. No. 09/959,770.

To differentiate various cucurbiturils, the inventors have adopted the term "cucurbit[n]uril", where n=4 to 12 and is the degree of polymerisation of the cucurbituril, that is, the number of glycoluril units or derivatives thereof included in the macrocyclic ring of the cucurbituril. For example, a cyclic oligomer having four glycoluril units, substituted or unsubstituted, joined together would be denoted as cucurbit [4]uril.

The term "unsubstituted cucurbituril" or "unsubstituted cucurbit[n]uril" refers to a cucurbituril in which $R_1$ and $R_2$ are both H in all the glycoluril units of formula II in the cucurbituril. The term "substituted cucurbituril" or "substituted cucurbit[n]uril" refers to a cucurbituril in which at least one of $R_1$ and $R_2$ is other than H for at least one glycoluril unit of formula II in the cucurbituril.

In accordance with the present invention, the cucurbit[n] uril may consist of some unsubstituted glycoluril units (i.e. where $R_1$ and $R_2$ are both H), and some substituted glycoluril units (i.e. where either or both of $R_1$ and $R_2$ are other than H). To differentiate such compounds, the term "cucurbit [s,u]uril" is used, where s equals the number of substituted glycolurils and u equals the number of unsubstituted glycoluril units, and s plus u equals 4 to 12.

Cucurbiturils have a central cavity which selectively encapsulates gases and volatile compounds.

The present invention in its preferred embodiments extends to the use of binding gases and volatile compounds in cucurbiturils for the following applications:
i) Stabilisation and/or storage wherein gases and volatiles can be contained in a solid structure for this purpose, and possible later release, for example, by dissolving the solid structure in a solvent and, if necessary, applying heat;
ii) Phase transfer catalysts for aqueous solutions thereby increasing the concentration of the gas in aqueous solution to 10 to 100 times above normal levels;
iii) Catalyse the reaction of a trapped gaseous or volatile species for the purposes of manufacturing chemical products;
iv) Trapping gaseous or volatile species during the manufacture of chemical products to render the species inactive;
v) Separation technologies allowing for the separation and purification of different gases or volatiles;
vi) Trapping of volatiles and gases, for example, from product gas streams for the purposes of recovery and/or removal, or from waste gas streams for the purposes of removal and/or recycling, or for removing unpleasant odours or toxic vapours;
vii) Drug delivery for the containment of biologically active ingredients to be released in a controlled manner or for the absorption of biologically active ingredients in order to control a biological outcome;
viii) Agricultural chemicals to provide a controlled release of active ingredients or the trapping of biologically active gases and volatile compounds to control or manipulate a biological outcome;
ix) Detection and analysis of some gases and volatiles by their pre-concentration and subsequent analysis; and
x) Combination systems of cucurbiturils and existing molecular systems such as the cyclodextrins when applied to any of the preceding applications.

According to preferred embodiments of the invention, the binding of gases and volatile compounds with cucurbit[n] urils (where n=5 to 10), and thereafter their release, can be effected in the following ways:
i) An aqueous solution of the cucurbit[n]uril is prepared, typically with a solubilising agent for increasing the solubility of the cucurbituril, such as metal salts, acids (mineral or organic), polyhydroxylated organic compounds including sugars (including polysugars such as cyclodextrins) or glycerol. The gas or volatile compound is passed through or absorbed into this aqueous solution to form a cucurbituril complex of the gas or volatile compound. Increased capacity of cucurbituril has been observed in the examples of unsubstituted cucurbit[5]uril where more than 1 mole equivalent of gas or volatile compound (the guest) was bound with the cucurbituril when sugars (for example glucose or cyclodextrins) were used as solubilising agents, where independently these sugars either have no binding capability or have limited ability. Isolation of the cucurbit[n]uril complex can be effected by crystallisation, evaporation of the solvent under atmosphere of the gas, or precipitation with a non-solubilising solvent such as MeOH.

The bound gas or volatile compound may be released from the cucurbituril complex in solution, by purging the complex with an inert gas such as nitrogen for an extended period and/or heating the complex. The complex may be purged with the inert gas by passing the inert gas through the solution containing the complex. Typically the complex is purged for more than 15 minutes and heated to between 60 to 100° C.

In the case where the cucurbituril complex has been isolated from the solution, the bound gas or volatile compound is typically released from the complex by dissolving the complex in a solvent at a temperature sufficient to release the gas or volatile compound. For unsubstituted cucurbit[n]uril complexes, the solvent is typically water, TFA or an aqueous salt solution, and the temperature is typically from 60 to 100° C.

ii) The cucurbit[n]uril is supported on a solid surface such as silica or alumina, or in a membrane where gases or volatile compounds can be separated, trapped, removed or released. The bound gas or volatile compound is typically released from the cucurbituril complex through diffusion of the gas or volatile compound from the complex.

iii) Gases or volatiles can be absorbed onto the solid cucurbit[n]uril without a matrix or support. Thereafter the gases or volatile compound can be released as required. In some embodiments, the bound gas or volatile compound may be released by purging the complex with an inert gas such as nitrogen for an extended period and/or heating the complex. More typically, the bound gas or volatile compound is released from the complex by dissolving the complex in a solvent at a temperature sufficient to release the gas or volatile compound.

For some cucurbituril complexes of a gas or volatile compound, there is a gradual diffusion of the bound gas or volatile compound from the complex. For such complexes, the bound gas or volatile compound may be released from the solid complex through this diffusion process.

Substituted cucurbit[n]urils can be used in the above embodiments. These substituted cucurbiturils may also be covalently bonded to a polymer attachment. These polymers may be membranes, beads or other solid or solution polymer forms.

The present inventors have found that unsubstituted cucurbit[6]uril, unsubstituted cucurbit[7]uril and hexamethylcucurbit[3,3]uril can bind dioxane. This dioxane binding property can form a basis of a process for removal of dioxane. Accordingly, in one embodiment, the invention provides a method of binding dioxane in a cucurbituril, said method comprising contacting the dioxane with unsubstituted cucurbit[6]uril, unsubstituted cucurbit[7]uril or hexamethylcucurbit[3,3]uril to form a cucurbituril complex of the dioxane. This method can be used to remove dioxane from a fluid.

The removal of dioxane could take place using one of the following techniques:

Unsubstituted Cucurbit[6 or 7]uril or hexamethylcucurbit [3,3]uril bound to a non-reactive solid support (silica or alumina) is mixed with the fluid containing the dioxane such that the dioxane binds to the cucurbit[6 or 7]uril or hexamethylcucurbit[3,3]uril, and is then removed from the fluid by simple filtration to collect the solid support.

A solution of unsubstituted cucurbit[6 or 7]uril or hexamethylcucurbit[3,3]uril partitioned by a membrane (for example a cellulose ester dialysis membrane) which allows the passage of dioxane into the solution where it is bound by the cucurbit[6 or 7]uril or hexamethylcucurbit[3,3]uril.

Incorporation of the unsubstituted cucurbit[6 or 7]uril or hexamethylcucurbit[3,3]uril into a solid clay support and use filtration techniques to remove bound dioxane.

Incorporation into a polymer film. In this case the dioxane is entrapped by the unsubstituted cucurbit[6 or 7]uril or hexamethylcucurbit[3,3]uril inside the polymer film. When the capacity of the film has been reached it is simply removed from the contact with the product steam.

In all cases the material itself could be regenerated for repeated use.

If the dioxane is contained in a solid, for example in dioxane/contaminated soil, the method may comprise the further step of washing the soil with a fluid to thereby cause the dioxane to go into the fluid and subsequently treating the fluid as described above.

The inventors have also found that unsubstituted cucurbit [5]uril uptakes carbon monoxide. Accordingly, in one embodiment, the present invention provides a method for binding carbon monoxide in a cucurbituril, said method comprising contacting the carbon monoxide with unsubstituted cucurbit[5]uril to form a cucurbituril complex of carbon monoxide. This method can be used to remove carbon monoxide from a liquid or from a mixture of gases containing carbon monoxide.

The following examples are provided in order to achieve a better understanding of the nature of the present invention although these examples are exemplary only.

1. Unsubstituted Cucurbit[n]urils and Substituted Cucurbit [s,u]urils as Solid Complexes i) Preparation of Solid Complexes

EXAMPLE 1

Saturated solutions of unsubstituted cucurbit[5]uril (approximately 6.8 gm/100 ml) in aqueous CsCl 0.2M or 5% $NH_4Cl$ solutions (approximately 15 gm/100 ml of unsubstituted cucurbit[5]uril) were prepared. A stream of acetylene was passed through the solutions (approximately 10 min at 20 mL/min) to reach saturation. Upon standing the crystalline product formed was collected at 15 to 30% yield. Alternatively, the solution was placed in an atmosphere of acetylene (ambient pressure to 3 atmospheres) and the reaction continued for 24 to 48 hours at 90% yield. Air-dried and weight stabilised samples showed negligible loss of acetylene after one (1) week. Loss of acetylene was also minimal up to 100° C. showing good thermal stability for the cucurbituril complex. The bound acetylene was detected by NMR by dissolving samples in aqueous salt solutions.

EXAMPLE 2

Saturated solutions of mixtures of dimethylcucurbit[1,4] uril and tetramethylcucurbit[2,3]uril (approximately 6 gm/100 ml) in aqueous CsCl 0.2M or 5% $NH_4Cl$ solutions (approximately 15 gm/100 ml of the cucurbit[s,u]uril) were prepared. A stream of acetylene was passed through the solutions (for approximately 10 min at 20 mL/min) to reach saturation. Upon standing the crystalline product formed was collected at 15 to 30% yield. Alternatively, the solution was placed in an atmosphere of acetylene (ambient pressure to 3 atmospheres) and the reaction continued for 24 to 48 hours at 90% yield. Air-dried and weight stabilised samples showed negligible loss of acetylene after one (1) week. Loss of acetylene was also minimal up to 100° C. The bound acetylene was detected by NMR by dissolving samples in aqueous salt solutions.

EXAMPLE 3

Saturated solutions of unsubstituted cucurbit[6]uril (approximately 6 gm/100 ml) in aqueous NaCl 1% or 5% $NH_4Cl$ solutions (approximately 15 gm/100 ml of unsubstituted cucurbit[6]uril) were prepared. A stream of propene was passed through the solutions to reach saturation (for approximately 10 min at 20 mL/min). Upon standing the crystalline product formed was collected at around 45% yield. Alternatively, the solution was placed in an atmosphere of propene (ambient pressure to 3 atmospheres) and the reaction continued for 24 to 48 hours at about 90% yield. The bound propene was observed by NMR by dissolving samples in aqueous salt solutions.

EXAMPLE 4

Saturated solutions of unsubstituted cucurbit[6]uril (approximately 6 gm/100 ml) in aqueous NaCl 1% or 5% $NH_4Cl$ solutions (approximately 15 gm/100 ml of cucurbit [6]uril) were prepared. A stream of isobutylene was passed through the solutions to reach saturation (for approximately 10 min at 20 mL/min). Upon standing the crystalline product formed was collected at 33% yield. Alternatively, the solution was placed in an atmosphere of propene (ambient pressure to 3 atmospheres) and the reaction continued for 24 to 48 hours at about 90% yield. The bound isobutylene was observed by NMR, of dissolved samples in $D_2O$ solutions.

EXAMPLE 5

A stream of carbon monoxide (20 mL/min) was passed through a solution of unsubstituted cucurbit[5]uril (45 mg) dissolved in trifluoroacetic acid (TFA) (0.6 ml) and the flow continued until all the TFA had evaporated to give the unsubstituted cucurbit[5]uril complex of CO at 95% yield. Alternatively, the solution was placed in a sealed container in an atmosphere of carbon monoxide and the solution of unsubstituted cucurbit[5]uril in TFA was placed above powdered NaOH. After 48 hours this yielded the solid unsubstituted cucurbit[5]uril complex of CO at about 50–65% yield. The complex and free unsubstituted cucurbit[5]uril were distinguished by a shift in the carbonyl resonance of $^{13}$C NMR spectra (magnitude 0.4 ppm). The same experiment was also carried out using $^{13}$C enriched carbon monoxide and its resonance observed.

EXAMPLE 6

A stream of carbon monoxide (20 mL/min) was passed through a solution of decamethylcucurbit[5]uril (45 mg) dissolved in TFA (0.6 ml) and the flow continued until all the TFA had evaporated to give the cucurbit[5]uril complex of CO at 95% yield. Alternatively, the solution was placed in a sealed container in an atmosphere of carbon monoxide and the solution of decamethylcucurbit[5]uril in TFA was placed above powdered NaOH. After 48 hours this yielded the solid cucurbituril complex at about 50–65% yield. The complex and free decamethylcucurbit[5]uril were distinguished by a shift in the carbonyl resonance of $^{13}$C NMR spectra (magnitude 0.4 ppm). The same experiment was also carried out using $^{13}$C enriched carbon monoxide and its resonance observed.

EXAMPLE 7

Saturated solutions of unsubstituted cucurbit[5]uril (approximately 6.8 gm/100 ml) in aqueous CsCl 0.2M or 5% NH$_4$Cl solutions (approximately 15 gm/100 ml of unsubstituted cucurbit[5]uril) were prepared, degassed by heating and purged with nitrogen. A stream of nitric oxide was passed through the cucurbituril solutions to reach saturation (for approximately 10 min at 20 mL/min). Upon standing a crystalline product was formed, which was collected at 40% yield. Alternatively, the solution was placed in an atmosphere of nitric oxide (ambient pressure to 3 atmospheres) and the reaction continued for 24 to 48 hours at about 90% yield. The influence of the bound nitric oxide was observed by NMR. D$_2$O salt solutions of the complex and free cucurbit[5]uril were distinguished by a shift in the carbonyl resonance of $^{13}$C NMR spectra (magnitude 0.3 ppm) and a similar shift in the methylene carbon resonances.

EXAMPLE 8

Saturated solutions of decamethylcucurbit[5]uril (approximately 6.8 gm/100 ml) in aqueous CsCl 0.2M were prepared, degassed by heating and purged with nitrogen. A stream of nitric oxide was passed through the solutions to reach saturation (for approximately 10 min at 20 mL/min). Upon standing the crystalline product was formed, which was collected at 40% yield. Alternatively, the solution was placed in an atmosphere of nitric oxide (ambient pressure to 3 atmospheres) and the reaction continued for 24 to 48 hours 90% yield. The influence of the bound nitric oxide was observed by NMR. D$_2$O salt solutions of the complex and free decamethylcucurbit[5]uril were distinguished by a shift in the carbonyl resonance of $^{13}$C NMR spectra (magnitude 0.3 ppm) and a similar shift in the methylene carbon resonances.

ii) Release of Gas or Volatiles from Solid Complexes

EXAMPLE 9

The unsubstituted cucurbit[5]uril complex of acetylene prepared as described in Example 1 was dissolved in hot water at 60 to 100° C. and the acetylene was released giving 100% yield of gas.

EXAMPLE 10

The method of Example 9 was also applied for the release of propene and isobutylene from solid complexes of unsubstituted cucurbit[6]uril and the respective gas prepared as described in Examples 3 and 4 respectively.

EXAMPLE 11

Carbon monoxide was released from either unsubstituted cucurbit[5]uril or decamethylcucurbit[5]uril solid complexes (prepared as described in Examples 5 and 6) by dissolving the complex in TFA or aqueous salt solutions and heating to 60 to 100° C. Complete recovery of gas was achieved.

EXAMPLE 12

The nitric oxide unsubstituted cucurbit[5]uril or decamethylcucurbit[5]uril complexes prepared as described in Examples 7 and 8 were dissolved in hot aqueous CsCl solutions releasing nitric oxide.

2. Preparation of Gas Complexes in Solution
   Hydrocarbon Gases

EXAMPLE 13

Unsubstituted cucurbit[5]uril or decamethylcucurbit[5]uril complexes of hydrocarbon gases including methane, ethylene and acetylene were prepared in aqueous solutions by dissolving unsubstituted cucurbit[5]uril or decamethylcucurbit[5]uril (50 mg) in aqueous CsCl 0.2M (0.6 ml) and passing a stream of the gas or a mixture of the gases through the solution. The formation of gas complexation was observed in the $^1$H NMR spectra characterised by an upfield shift of 0.8 ppm of the complexed gas proton resonances compared to the uncomplexed gas protons.

EXAMPLE 14

Unsubstituted cucurbit[6]uril complexes of hydrocarbon gases including methane, propane, propene, ethane, butane, isobutane, isobutylene and butadiene were prepared in aqueous solutions by dissolving unsubstituted cucurbit[6]uril (50 mg) in CsCl 0.2M (0.6 ml) and passing a stream of the gas or a mixture of the gases through the solution. The formation of gas complexation was observed in the $^1$H NMR spectra characterised by an upfield shift of 0.6 to 0.8 ppm of the complexed gas proton resonances compared to the uncomplexed gas protons.

Inorganic Gases

EXAMPLE 15

Unsubstituted cucurbit[5]uril or decamethylcucurbit[5]uril complexes of inorganic gases including N$_2$, O$_2$, Ar, Ne, CO and NO were prepared in aqueous solutions by dissolving unsubstituted cucurbit[5]uril or decamethylcucurbit[5]uril (50 mg) in aqueous CsCl 0.2M (0.6 ml) and passing a stream of the gas or a mixture of the gases through the solution. The formation of gas complexation was observed in the $^{13}$C NMR spectra characterised by a downfield shift of 0.2 to 0.6 ppm of the carbonyl carbon resonances of the complex. Gas complexes of substituted cucurbit[s,u]uril have also been observed in Electrospray mass spectra, for example mixtures of $Ph_sMe_s$cucurbit[s,u]uril where s=1 to 4 and u=4 to 1.

EXAMPLE 16

Unsubstituted cucurbit[6]uril (1 g) was dissolved in aqueous NaCl 0.2M (25 ml) and a bubbler fitted with a frit was inserted into the solution so that, under applied low vacuum, air was drawn through the solution at 1 L/min. Attached by a short path to the intake was a preweighed vessel (the carrier) containing iodine crystals. Under vacuum the iodine vapour was drawn through the cucurbit[6]uril solution and at the point when iodine was first detected at the exhaust vent of the cucurbit[6]uril solution, the uptake of iodine was measured. The uptake was determined by measuring the iodine weight lost from the carrier which was equal to the iodine adsorb by the cucurbit[6]uril solution. A mole weight of 10% was measured.

EXAMPLE 17

The experiment of Example 16 was carried out using solid unsubstituted cucurbit[6]uril (1 g), activated at 150° C. in vacuo or without activation and dry iodine gas was passed through the solid (flows of 100 mL/min and 1 L/min) until iodine was detected in the exhaust. Saturation of samples without activation at 100 mL/min was 5%, or at 1 L/min was 2%. Saturation of activated samples at 100 mL/min was 35%, or at 1 L/min was 10%.

3. Separation of Hydrocarbon Gases using Aqueous Solution

EXAMPLE 18

The Separation of Propane from Natural Gas (Initial Proportion of Propane 0.15% and Ethane 4%)

An aqueous solution of CsCl 0.2M (0.6 mL) and unsubstituted cucurbit[6]uril (50 mg) was prepared and natural gas passed through (at 20 mL/min) the solution for 1 to 5 minutes. The solution was then purged with nitrogen (at 20 mL/min) for 30 to 90 seconds to remove methane and ethane. The propane was then recovered at 98 to 99% purity by either purging with nitrogen for 20 minutes or heating to 60 to 100° C. By removing some of the propane from the natural gas, higher purity methane is obtained.

EXAMPLE 19

Ethane, Propane Enrichment by Concentration from Methane.

A two chamber process where in chamber 1 an aqueous solution of CsCl 0.2M (6 mL) and cucurbit[5]uril (500 mg) was prepared and natural gas passed through (20 mL/min) the solution for 1 to 5 minutes. The majority of methane in the natural gas was retained by the solution in chamber 1. In chamber 2 the exhaust of chamber 1 was passed through an aqueous solution of CsCl 0.2M (1.2 mL) and unsubstituted cucurbit[6]uril (100 mg). The solution of unsubstituted cucurbit[6]uril in chamber 2 was purged with nitrogen (at 20 mL/min) for 30 to 90 seconds to remove any residual methane and ethane (ethane 40 to 60% purity). The propane was then recovered from chamber 2 at 98 to 99% pure by either purging with nitrogen for 20 minutes or heating to 60 to 100° C.

EXAMPLE 20

Separation of Propane from Propane/Isobutane Mixture.

An aqueous solution of $C_sCl$ 0.2M (0.6 mL) and unsubstituted cucurbit[6]uril (50 mg) was prepared and a 1:1 mixture of propane and isobutane was passed through (at 20 mL/min) the solution for 1 to 5 minutes. The solution was then purged with nitrogen (at 20 mL/min) up to 5 minutes to separate propane at purity of 80%. As a consequence of the removal of propane, isobutane is purified.

EXAMPLE 21

Separation of Propene from Propene/Propane Mixture.

An aqueous solution of CsCl 0.2M (0.6 mL) and unsubstituted cucurbit[6]uril (50 mg) was prepared and a 1:1 mixture of propane and propene was passed through (at 20 mL/min) the solution to reach saturation (for approximately 10 minutes). Upon standing the unsubstituted curbit[6]uril complex of propene crystallised. This product was collected at 15 to 20 mg. The propene was then recovered 98 to 99% pure by dissolving the complex in water at 60 to 100° C. and either purging with nitrogen for 20 minutes or continued heating. As a consequence of the removal of propene, propane is purified.

EXAMPLE 22

Separation of Isobutylene from Isobutylene/Isobutane Mixture.

An aqueous solution of CsCl 0.2M (0.6 mL) and unsubstituted cucurbit[6]uril (50 mg) was prepared and a 1:1 mixture of isobutylene and isobutane was passed through (at 20 mL/min) the solution to reach saturation (for approximately 10 minutes). Upon standing the unsubstituted cucurbit[6]uril complex of isobutylene crystallised. This product was collected at 15 to 20 mg. The isobutylene was then recovered 98 to 99% pure by dissolving the complex in water at 60 to 100° C. and either purging with nitrogen for 20 minutes or continued heating. As a consequence of the removal of isobutylene, isobutane is purified.

4. Separation of Gases using Cucurbit[n]urils and Substituted Cucurbit[s,u]urils in the Solid Phase in a GLC Column

EXAMPLE 23

A Silica Supported Cucurbit[n]uril Column.

A mixture of unsubstituted cucurbit[5]uril, unsubstituted cucurbit[6]uril, unsubstituted cucurbit[7]uril and unsubstituted eucurbit[8]uril in a ratio of 20:50:22:8 (2 gm) was dissolved in 32% HCl and silica gel (100 g) added. The water and HCl were removed from the mixture in vacuo and then the mixture dried at 80° C. Two columns were prepared, one with the above support and the second with silica gel only. The columns were conditioned over 24 hours with a continuous flow of He at 100° C. Samples of gases were then compared for their separation on each of these columns at ambient to 50° C. At, ambient temperature air, or $N_2$ and $O_2$ retention of 2.1 min $O_2$ as a late shoulder, CO 3 min. At 50° C. $C_2H_2$, $C_2H_4$, $C_3H_8$ etc after 15 min. The retention times were up to and greater than 1 minute longer on the cucurbit[n]uril supported column compared to the silica column.

5. Solid-phase Adsorption and Desorption (Malodours, Fragrances, Volatiles, Gases)

Two studies were undertaken; namely:
i) the adsorption of some volatile or gaseous guests onto activated solid samples of each of the pure unsubstituted cucurbit[n]urils, under high vacuum was measured, primarily over a 1 hour period; and
ii) The adsorption of selected volatile or gaseous guests onto stabilised, solid samples of pure unsubstituted cucurbit[n]urils, over a 20 hour period was measured and thereafter desorption was measured over a 1 hour period under a flow of nitrogen (at 100 mL/min).

EXAMPLE 24

Adsorption into pure samples of unsubstituted cucurbit [5–7]urils (250 mg) of the specified volatile compounds listed in the table below were examined using a Cahn Microbalance in a vacuum/vapour chamber. Under these conditions, the pressure of the volatile guests is effectively the vapour pressure of the guest. The unsubstituted cucurbit[5–7]uril were prepared by pre-drying at 150° C. in vacuo at 0.1 mmHg over 12 hours. No attention was given to particle size other than the visual appearance was of a fine powder. Weighed samples in pans were placed on the microbalance and the chamber evacuated to 0.1 mmHg and pumping continued until a stable weight was obtained at room temperature (approximately 25° C.). At this point, previously degassed (freeze-thaw method) volatile samples were opened to the evacuated chamber and the weight gains were monitored (chart recorder) over a 1 hour period. In some cases, where time permitted, monitoring was continued over several hours.

TABLE 1

Adsorption of volatiles into cucurbit[5 to 7]urils

| Volatile Guest | Cucurbit[5 to 7]uril host Mole Weight % Gain | | |
|---|---|---|---|
| | Q5 | Q6 | Q7 |
| Diethyltoluamide (DET)* | — | 29 | 10 |
| | | | 109 19 hr |
| Citronellal | — | 23 | 5 |
| Dipropylene glycol | — | 21 | 8 |
| | | 144 17 hr | |
| N-methylmorpholine | — | 48 | 7 |
| | | | 212 64 hr |
| Napthalene-2-thiol | — | 8 | 4 |
| Ethyl mercaptan | 29 | 179 | — |
| 2-phenylethanol | — | — | 10 |
| | | | 69 20 hr |
| Dioxane | 36 | 133 | 35 |
| Methylisothiocyanate | 15 | 173 | 34 |
| Phenylisothiocyanate | — | 14 | 9 |
| | | 56 18 hr | 33 18 hr |
| Propene | 48 | 171 | 29 |

The percent weight gain shown in Table 1 was determined as the amount taken up by the solid host divided by the theoretical amount possible (assuming a 1:1 complex)×100. Unless otherwise stated, weight changes were monitored over a 1 hour time period. In all cases, the maximum uptake had not been reached at the times shown in Table 1. Maximum uptake would appear to be greater than 1 mole equivalent.

The inventors have also found that cucurbit[8]uril absorbs DET, both as a solid and a solution.

EXAMPLE 25

Samples of unsubstituted cucurbit[5 to 7]urils (250 mg) were stabilised to constant weight by placing them together in a desiccator and purging with dry nitrogen gas at a rate of 100 mL/min for 72 hours. One sample of each cucurbit[n] uril was weighed and placed in a sealed desiccator containing a vial of one of the volatile potential guests. This procedure was repeated for each of the volatile substances in Table 2.

After a 20 hour adsorption period at atmospheric pressure, the samples were removed and weighed to determine the weight gain, then returned to the desiccator and a stream of dry nitrogen applied at 100 mL/min for 1 hour and the samples weighed again to determine weight loss. It was not possible to obtain saturation of all the volatile guests by each host in a reasonable time frame. Because the volatile guests are absorbed at different rates into the various hosts, for comparative purposes the 1 hour weight loss (under nitrogen flow) is reported as a percentage of the 20 hour weight gain (at the vapour pressure of the guest in a sealed desiccator) in Table 2.

TABLE 2

Adsorption of volatiles into cucurbit[5 to 7]urils

| Volatile guest | 20 hr % gain 1 hr % loss | Cucurbit[5 to 7]uril host | | |
|---|---|---|---|---|
| | | Q6 | Q7 | Q5 |
| N, N-diethyl-m-toluamide (DET) | Gain | 30 | 73 | — |
| | loss | <2 | <2 | |
| Citronellal | Gain | 29 | 30 | — |
| | loss | <2 | <2 | |
| Dipropylene glycol | Gain | 26 | 1 | — |
| | loss | <2 | <2 | |
| N-methylmorpholine | Gain | 44 | 100 | — |
| | loss | 49 | 18 | |
| Napthalene-2-thiol | Gain | 23 | 25 | — |
| | loss | <2 | <2 | |
| ethanethiol | Gain | 60 | 95 | <2 |
| | loss | 15 | 4 | |

The percentage weight gain over 20 hours was determined as the amount taken up by the solid, divided by the theoretical amount possible (assuming a 1:1 complex)×100. Losses marked (<2) were too small to record with any reliability in the 1 hour period of nitrogen gas flow and in some of these cases weight gains (<2%) were observed, suggesting $N_2$ or $H_2O$ adsorption which was influenced by the guest.

Table 3 indicates the results of gas phase modelling studies of potential guests for unsubstituted cucurbit[5 to 7]urils. The guests are relatively small molecules.

TABLE 3

Gas-phase modelling of cucurbit[5 to 7]uril

| Gas or Volatile Guest | Cucurbit[5 to 7]uril Host | | |
|---|---|---|---|
| | Q5 | Q6 | Q7 |
| Pesticides | | | |
| Triclabendazole | | ✓ | ✓✓ |
| Trifluramon | | ✓ | ✓✓ |
| Cyromazine | | ✓ | ✓✓ |
| Famphur | | ✓✓ | ✓✓ |
| Fenthion | | ✓ | ✓✓ |
| Vet. Antibiotics | | | |
| Omeprazole | | | ✓ |
| Bifonazole | | | ✓✓ |
| Gases | | | |
| NO | ✓ | ✓ | |
| Acetylene | ✓ | ✓ | |
| $H_2S$ | ✓ | | |
| butane | | ✓✓ | |
| sevoflurane | | | ✓ |
| Isoflurane | | | ✓ |
| desflurane | | | ✓ |
| Halothane | | ✓ | ✓✓ |
| Fragrances/odors | | | |
| Phenylethyl alcohol (rose oil) | | ✓ | ✓ |
| Pulegone (peppermint) | | ✓ | ✓✓ |
| Allicin (garlic) | | ✓ | |
| Cls-Jasmone (jasmine) | | ✓ | ✓✓ |

TABLE 3-continued

Gas-phase modelling of cucurbit[5 to 7]uril

| Gas or Volatile Guest | Cucurbit[5 to 7]uril Host | | |
|---|---|---|---|
| | Q5 | Q6 | Q7 |
| Geranyl formate (rose smell) | | ✓ | ✓✓ |

✓ = 0–20 kcal/mol better inside than out by MM+ molecular mechanics modelling
✓✓ = >20 kcal/mol better inside than out by MM+ molecular mechanics modelling Gas phase modelling of $H_2$ for unsubstituted cucurbit[4]uril indicates $H_2$ is 0–20 kcal/mol better inside than out by MM+ molecular mechanics modelling.

INDUSTRIAL APPLICABILITY

The potential uses for cucurbit[n]urils are large with academic, industrial, analytical and pharmaceutical applications. As a class these molecules can be favourable compared to the cyclodextrins because both molecular systems posses a hydrophobic cavity with polar end caps. Cyclodextrins have been used in a wide range of applications including slow release drugs, odour entrapment agents in plastic films, and enzimimics for synthesis. It is believed that cucurbit[n]urils will be of use in similar areas where benefit can be taken of the ability of the cucurbit[n]urils to take up molecules or compounds into their central cavity. Such potential uses may include:

Environmental (Water and Soil)
Remediation, by the binding of polluting products and their removal:
  Preventative, eg, by binding of potential pollutants before wastes are released to the environment;
  Uses in biodegradable polymers.
Domestic and Public
  Incorporation into polymers as odourisers, releasing fragrances slowly over time;
  Or incorporated into polymers to trap unpleasant odours or toxic vapours
  Encapsulation of bleaching and whitening agents.
Food
  Flavour enhancers;
  Flavour optimisers, hence hiding unpleasant flavours:
  Polyphenol removal to reduce discolouration of juices.
Pharmaceutical
  Slow release drugs, limiting side effects and reducing the frequency of doses;
  Increasing drug stability in vivo or on the shelf;
  Detoxification, for example, decreasing stomach irritations, or the treatment of chemical allergens by encapsulation.
Agricultural/Horticultural
  Slow release of herbicides and pesticides;
  Stabilisation of agricultural chemicals against light and heat.
Manufacturing
  Enzyme/catalyst mimics;
  Regioselective control over reaction products;
  Manipulation of paint and polymer products;
  Chromatographic columns for chemical purification;
  Analytical tools and devices;
  Printing and photography.
Miscellaneous
  Volatility reduction, for storage, safety, or use;
  Uses for insensitive munitions manufacture;
  Forensic science.

Cucurbit[n]urils are thermally more robust than cyclodextrins and are stable to strong acid solutions unlike cyclodextrins.

The present inventors have also found that cucurbit[6]uril and cucurbit[7]uril can both bind dioxane aqueous solutions. This dioxane binding property can form the basis of processes for the removal of dioxane. According to a further aspect of the present invention, the present invention provides a process for removing dioxane from a fluid comprising contacting the fluid with cucurbit[6]uril and/or cucurbit[7]uril.

The physical removal of dioxane could take place using one of the following techniques:
  Cucurbit[6 or 7]uril bound to a non-reactive solid support (silica or alumina) where the dioxane would bind to the cucurbit[6 or 7]uril and then be removed from solution by simple filtration to collect the solid support.
  A solution of cucurbit[6 or 7]uril placed in dialysis tubing which would allow the passage of dioxane into the solution where it would be bound by the cucurbit[6 or 7]uril.
  Incorporation of the cucurbit[6 or 7]uril into a solid clay support and use filtration techniques to remove bound dioxane.
  Incorporation into a polymer film. In this case the dioxane would be entrapped by the cucurbit[6 or 7]uril inside the polymer film. When the capacity of the film has been reached it is simply removed from contact with the product stream.
  In all cases the material itself could be regenerated for repeated use.

If the dioxane is contained in the solid, for example in dioxane/contaminated soil, the process of this aspect of the invention may comprise the further step of washing the soil with a fluid to thereby cause the dioxane to go into the fluid and subsequently treating the fluid in accordance with this aspect of the invention.

Cucurbit[5]uril has shown uptake of carbon monoxide. Accordingly, the invention further provides a method for removing carbon monoxide from a liquid or vapour containing carbon monoxide by contacting the liquid or vapour with cucurbit[5]uril.

It should be readily apparent to those skilled in the art that the invention described herein is susceptible to variations and modifications other than those specifically described. For example, the invention is not limited to the cucurbiturils or gases or volatile compounds for which experiments have been reported but rather extends to all cucurbiturils and gases or volatile compounds broadly encompassed by the invention. The gas or volatile compound, or the mixture of compounds including the gas or volatile compound, may be contacted with a cucurbituril by virtually any means and the invention is not restricted to the specific methods of contact exemplified in the examples. Furthermore, the invention is not limited to the experimental techniques used in releasing the bound gas or volatile compounds from the cucurbituril complex.

All such variations and modifications are to be considered within the scope of the present invention the nature of which is to be determined from the foregoing description.

It is to be understood that a reference herein to a prior art document does not constitute an admission that the document forms part of the common general knowledge in the art in the United States or of in any other country.

What is claimed is:

1. A method of binding a gas in a cucurbituril, said method comprising contacting the gas with the cucurbituril to form a cucurbituril complex of the gas.

2. A method according to claim 1 wherein the cucurbituril is in solution and the gas is contacted with the cucurbituril by passing the gas through the solution containing the cucurbituril.

3. A method according to claim 2 wherein the cucurbituril is in an aqueous solution.

4. A method according to claim 3 wherein the aqueous solution comprises a solubilising agent for increasing the solubility of the cucurbituril in the aqueous solution.

5. A method according to claim 4 wherein the solubilising agent is selected from the group consisting of metal salts, ammonium salts, acids and polyhydroxylated organic compounds.

6. A method according to claim 1 wherein the gas is the gaseous phase of a volatile compound.

7. A method according to claim 1 wherein the cucurbituril is a solid.

8. A method of separating a gas from a gaseous mixture of compounds containing the gas, said method comprising the steps of:
   1) contacting the mixture with a cucurbituril whereby at least some of the gas is bound to the cucurbituril to form a cucurbituril complex of the gas; and
   2) releasing at least some of the bound gas from the complex.

9. A method according to claim 8 wherein, in step 1), the cucurbituril is in solution and the mixture is contacted with the cucurbituril by passing the mixture through the solution containing the cucurbituril.

10. A method according to claim 9 wherein the cucurbituril is in an aqueous solution.

11. A method according to claim 10 wherein the aqueous solution comprises a solubilising agent for increasing the solubility of the cucurbituril in the aqueous solution.

12. A method according to claim 11 wherein the solubilising agent is selected from the group consisting of metal salts, ammonium salts, acids and polyhydroxylated organic compounds.

13. A method according to claim 8 wherein the gas is the gaseous phase of a volatile compound.

14. A method according to claim 8 wherein the cucurbituril is a solid.

15. A method according to claim 14 wherein the gas is released from the complex by dissolving the complex in a solvent and heating the resultant solution to release the gas from the complex.

16. A method of binding acetylene in a cucurbituril, said method comprising contacting acetylene with a cucurbituril selected from the group consisting of unsubstituted cucurbit[5]uril, decamethylcucurbit[5]uril, dimethylcucurbit[1,4]uril and tetramethylcucurbit[2,3]uril, to form a cucurbituril complex of acetylene.

17. A method of binding dioxane in a cucurbituril, said method comprising contacting dioxane with a cucurbituril selected from the group consisting of unsubstituted cucurbit[6]uril, unsubstituted cucurbit[7]uril and hexamethylcucurbit[3,3]uril, to form a cucurbituril complex of dioxane.

18. A method of binding carbon monoxide in a cucurbituril, said method comprising contacting carbon monoxide with unsubstituted cucurbit[5]uril to form a cucurbituril complex of carbon monoxide.

* * * * *